(12) United States Patent
Hwang et al.

(10) Patent No.: US 11,701,009 B2
(45) Date of Patent: Jul. 18, 2023

(54) APPARATUS AND METHOD FOR MEASURING BIO-INFORMATION

(71) Applicant: SAMSUNG ELECTRONICS CO., LTD., Suwon-si (KR)

(72) Inventors: Jeong Eun Hwang, Suwon-si (KR); Byung Hoon Ko, Hwaseong-si (KR); Chang Mok Choi, Suwon-si (KR); Sang Yun Park, Hwaseong-si (KR); Jong Wook Lee, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 637 days.

(21) Appl. No.: 16/740,591

(22) Filed: Jan. 13, 2020

(65) Prior Publication Data
US 2020/0288995 A1  Sep. 17, 2020

(30) Foreign Application Priority Data

Mar. 15, 2019  (KR) .................. 10-2019-0030174
Aug. 20, 2019  (KR) .................. 10-2019-0101838

(51) Int. Cl.
*A61B 5/1455*  (2006.01)
*A61B 5/021*  (2006.01)
(Continued)

(52) U.S. Cl.
CPC ...... *A61B 5/02108* (2013.01); *A61B 5/02007* (2013.01); *A61B 5/0261* (2013.01);
(Continued)

(58) Field of Classification Search
CPC ...... A61B 5/1455; A61B 5/02; A61B 5/14532
See application file for complete search history.

(56) References Cited

U.S. PATENT DOCUMENTS 9,826,912 B2  11/2017  Ungureanu et al.
2008/0154104 A1  6/2008  Lamego et al.
(Continued)

FOREIGN PATENT DOCUMENTS

EP  3552539 A1  10/2019
EP  3 818 930 A1  5/2021
(Continued)

OTHER PUBLICATIONS

Communication dated Aug. 17, 2021, issued by the European Patent Office in European Application No. 20162972.2.
(Continued)

*Primary Examiner* — Marjan Fardanesh
(74) *Attorney, Agent, or Firm* — Sughrue Mion, PLLC

(57) ABSTRACT

An apparatus for measuring bio-information may include: a pulse wave sensor comprising at least one pair of light emitters which are disposed apart from each other and a light receiver disposed between the at least one pair of light emitters, and configured to measure a plurality of pulse wave signals from an object by using the light receiver and the at least one pair of light emitters; a force sensor configured to measure a contact force that is applied to the pulse wave sensor by the object; and a processor configured to generate an integrated pulse wave signal by integrating the plurality of pulse wave signals based on the contact force and an area of a contact surface of the pulse wave sensor, and estimate bio-information of the object based on the integrated pulse wave signal.

16 Claims, 15 Drawing Sheets

(51) Int. Cl.
  *A61B 5/02* (2006.01)
  *A61B 5/024* (2006.01)
  *A61B 5/026* (2006.01)
  *A61B 5/145* (2006.01)
  *A61B 5/00* (2006.01)

(52) U.S. Cl.
  CPC ........ *A61B 5/02427* (2013.01); *A61B 5/1455* (2013.01); *A61B 5/14532* (2013.01); *A61B 5/681* (2013.01); *A61B 5/6843* (2013.01); *A61B 5/6897* (2013.01); *A61B 5/6898* (2013.01)

(56) References Cited

U.S. PATENT DOCUMENTS

| | | |
|---|---|---|
| 2016/0278645 A1 | 9/2016 | Yoon |
| 2017/0095168 A1 | 4/2017 | Kwon et al. |
| 2017/0119262 A1 | 5/2017 | Shim et al. |
| 2017/0127958 A1 | 5/2017 | Ungureanu |
| 2017/0360374 A1 | 12/2017 | Elliot et al. |
| 2018/0177413 A1 | 6/2018 | Kwon et al. |
| 2019/0105001 A1* | 4/2019 | Newberry ............ A61B 5/0002 |
| 2019/0313979 A1 | 10/2019 | Kang et al. |
| 2020/0383641 A1 | 12/2020 | Hwang et al. |

FOREIGN PATENT DOCUMENTS

| | | |
|---|---|---|
| JP | 2011-254957 A | 12/2011 |
| KR | 10-2006-0116635 A | 11/2006 |
| KR | 10-2014-0130272 A | 11/2014 |
| KR | 10-2016-0115017 A | 10/2016 |
| KR | 10-2017-0040034 A | 4/2017 |
| KR | 10-2017-0049279 A | 5/2017 |
| KR | 10-2018-0076050 A | 7/2018 |
| KR | 10-2019-0119414 A | 10/2019 |
| KR | 10-2020-0005445 A | 1/2020 |
| WO | 2016135731 A1 | 9/2016 |
| WO | 2017152098 A1 | 9/2017 |
| WO | 2020009496 A1 | 1/2020 |

OTHER PUBLICATIONS

Xiaoyin Zhu, "Tutorial on Hertz Contact Stress", OPTI 521, Dec. 1, 2012 (8 pages total).

Communication dated May 4, 2020, issued by the European Patent Office in counterpart European Application No. 20162972.2.

* cited by examiner

APPARATUS AND METHOD FOR MEASURING BIO-INFORMATION

CROSS-REFERENCE TO RELATED APPLICATION(S)

This application claims priority from Korean Patent Application No. 10-2019-0030174, filed on Mar. 15, 2019, and Korean Patent Application No. 10-2019-0101838, filed on Aug. 20, 2019, in the Korean Intellectual Property Office, the disclosures of which are incorporated herein by reference in their entireties.

BACKGROUND

1. Field

Apparatuses and methods consistent with example embodiments relate to measuring bio-information.

2. Description of the Related Art

A pressurized cuff is generally used for measuring blood pressure. A blood pressure measuring method utilizing the pressurized cuff is a non-continuous measuring method, in which the blood pressure is measured when the cuff is slowly released after being inflated until an arterial pressure reaches a maximum value. However, the pressurized cuff may require a pressure pump and therefore may not be suitable for use in a small mobile device.

Recently, research has been conducted on blood pressure measuring apparatuses for cufflessly measuring blood pressure in a non-pressure manner without using a cuff, and examples thereof include a blood pressure measuring apparatus using Pulse Transit Time (PTT) and a blood pressure measuring apparatus using Pulse Wave Analysis (PWA). However, the blood pressure measuring apparatus using PTT is inconvenient in that correction is required for each user to ensure accuracy of measurement; and since bio-signals should be measured at two or more positions to measure the pulse wave velocity, the apparatus cannot be manufactured in a compact size. Further, the blood pressure measuring apparatus using PWA estimates blood pressure by analyzing only a pulse waveform, such that the PWA is vulnerable to noise, and blood pressure may not be measured accurately.

SUMMARY

Example embodiments provide an apparatus and method for measuring bio-information.

According to an aspect of an example embodiment, there is provided an apparatus for measuring bio-information, the apparatus including: a pulse wave sensor comprising at least one pair of light emitters which are disposed apart from each other and a light receiver disposed between the at least one pair of light emitters, the pulse wave sensor being configured to measure a plurality of pulse wave signals from an object by using the light receiver and the at least one pair of light emitters; a force sensor configured to measure a contact force that is exerted to the pulse wave sensor by the object; and a processor configured to generate an integrated pulse wave signal by integrating the plurality of pulse wave signals based on the contact force and an area of a contact surface of the pulse wave sensor, and estimate bio-information of the object based on the integrated pulse wave signal.

The contact surface of the pulse wave sensor may be formed as a curved surface, and an entire surface of the contact surface may be configured to be in contact with the object.

The light receiver may be disposed under the curved surface and aligned at a center of the curved surface.

The at least one pair of light emitters may be disposed in a longitudinal direction of the pulse wave sensor or in a tangential direction of the curved surface.

The area of the contact surface may be less than an average area of a type of the object.

The processor may be further configured to determine a center of the contact force, and integrate the plurality of pulse wave signals by applying a weight to each of the plurality of pulse wave signals based on the determined center of the contact force.

The at least one pair of light emitters may include a first light emitter and a second light emitter, and the first light emitter is disposed at a first position having a greater contact force than a second position at which the second light emitter is disposed, wherein the plurality of pulse wave signals may include a first pulse wave signal measured by using the first light emitter and a second pulse wave signal measured by using the second light emitter, and wherein the processor may be further configured to apply a first weight to the first pulse wave signal that is measured by using the first light emitter located at the first position having the greater contact force, and apply a second weight to the second pulse wave signal that is measured by using the second light emitter located at the second position having a smaller contact force, the first weight being greater than the second weight.

The processor may be further configured to generate the integrated pulse wave signal by applying the weight to each of the plurality of pulse wave signals to obtain weighed pulse wave signals, and by summing up the weighted pulse wave signals.

The plurality of pulse wave signals may be photoplethysmogram (PPG) signals.

The processor may be further configured to generate guide information on a recommended contact force based on the contact force which is measured by the force sensor.

The bio-information comprises at least one of blood pressure, blood glucose, cholesterol, vascular age, arterial stiffness, aortic pressure waveform, vascular compliance, blood triglyceride, cardiac output, total peripheral resistance, stress index, and degree of fatigue.

According to an aspect of another example embodiment, there is provided an apparatus for measuring bio-information, including: a pulse wave sensor comprising at least one pair of light emitters which are disposed apart from each other and a light receiver disposed between the at least one pair of light emitters, the pulse wave sensor being configured to measure a plurality of pulse wave signals from an object by using the light receiver and the at least one pair of light emitters; a force distribution sensor configured to measure a contact force distribution of a contact force that is exerted to a contact surface of the pulse wave sensor by the object and is distributed along the contact surface of the pulse wave sensor; and a processor configured to generate an integrated pulse wave signal by integrating the plurality of pulse wave signals based on the contact force distribution, and estimate bio-information of the object based on the integrated pulse wave signal.

The contact surface of the pulse wave sensor may be formed as a curved surface, and an entire surface of the contact surface is configured to be in contact with the object.

The light receiver may be disposed under the curved surface and aligned at a center of the curved surface.

The at least one pair of light emitters may be disposed in a longitudinal direction of the pulse wave sensor or in a tangential direction of the curved surface.

An area of the contact surface may be less than an average area of a type of the object.

The processor may be further configured to integrate the plurality of pulse wave signals by applying a weight to each of the plurality of pulse wave signals based on the contact force distribution.

The at least one pair of light emitters may include a first light emitter and a second light emitter, and the first light emitter is disposed at a first position having a greater contact force than a second position at which the second light emitter is disposed, wherein the plurality of pulse wave signals may include a first pulse wave signal measured by using the first light emitter and a second pulse wave signal measured by using the second light emitter, and wherein the processor may be further configured to apply a first weight to the first pulse wave signal that is measured by using the first light emitter located at the first position having the greater contact force, and apply a second weight to the second pulse wave signal that is measured by using the second light emitter located at the second position having a smaller contact force, the first weight being greater than the second weight.

The processor may be further configured to generate the integrated pulse wave signal by applying the weight to each of the plurality of pulse wave signals to obtain weighted pulse wave signals, and by summing up the weighted pulse wave signals.

The plurality of pulse wave signals may be photoplethysmogram (PPG).

The processor may be further configured to generate guide information on a recommended contact force based on the contact force which is measured while the plurality of pulse wave signals are measured.

The bio-information may include at least one of blood pressure, blood glucose, cholesterol, vascular age, arterial stiffness, aortic pressure waveform, vascular compliance, blood triglyceride, cardiac output, total peripheral resistance, stress index, and degree of fatigue.

According to an aspect of another example embodiment, there is provided a method of measuring bio-information, including: measuring, by a pulse wave sensor, a plurality of pulse wave signals from an object, the pulse wave sensor comprising at least one pair of light emitters which are disposed apart from each other and a light receiver disposed between the at least one pair of light emitters; measuring a contact force that is exerted to the pulse wave sensor by the object; generating an integrated pulse wave signal by integrating the plurality of pulse wave signals based on the contact force and an area of a contact surface of the pulse wave sensor; and estimating bio-information of the object based on the integrated pulse wave signal.

The generating the integrated pulse wave signal may include: determining a center of the contact force; and integrating the plurality of pulse wave signals by applying a weight to each of the plurality of pulse wave signals based on the determined center of the contact force.

The measuring the plurality of pulse wave signals may include measuring a first pulse wave signal by using a first light emitter of the pair of light emitters and the light receiver, and measuring a second pulse wave signal by using a second light emitter of the pair of light emitters, wherein the first light emitter be disposed closer to the center of the contact force than the second light emitter, and wherein the integrating the plurality of pulse wave signals may include applying a first weight to the first pulse wave signal that is measured by using the first light emitter which is located closer to the center of the contact force, and applying a second weight to the second pulse wave signal measured by using the second light emitter which is located further from the center of the contact force than the first light emitter, the first weight being greater than the second weight.

The integrating the plurality of pulse wave signals may include applying the weight to each of the plurality of pulse wave signals to obtain weighted pulse wave signals, and by summing up the weighted pulse wave signals.

The plurality of pulse wave signals may be photoplethysmogram (PPG) signals.

The bio-information may include at least one of blood pressure, blood glucose, cholesterol, vascular age, arterial stiffness, aortic pressure waveform, vascular compliance, blood triglyceride, cardiac output, total peripheral resistance, stress index, and degree of fatigue.

According to an aspect of another example embodiment, there is provided a method of measuring bio-information, including: measuring, by a pulse wave sensor, a plurality of pulse wave signals from an object, the pulse wave sensor comprising at least one pair of light emitters which are disposed apart from each other and a light receiver disposed between the at least one pair of light emitters; measuring a contact force distribution of a contact force that is exerted to a contact surface of the pulse wave sensor by the object and is distributed along the contact surface of the pulse wave sensor; generating an integrated pulse wave signal by integrating the plurality of pulse wave signals based on the contact force distribution; and estimating bio-information of the object based on the integrated pulse wave signal.

The generating the integrated pulse wave signal may include integrating the plurality of pulse wave signals by applying a weight to each of the plurality of pulse wave signals based on the contact force distribution.

The measuring the plurality of pulse wave signals may include measuring a first pulse wave signal by using a first light emitter of the pair of light emitters and the light receiver, and measuring a second pulse wave signal by using a second light emitter of the pair of light emitters and the light receiver. The generating the integrated pulse wave signal may include integrating the plurality of pulse wave signals by applying a first weight to the first pulse wave signal that is measured by using the first light emitter located at a first position having a greater contact force than a second position where the second light emitter is located, and applying a second weight to the second pulse wave signal measured by using the second light emitter located at the second position, the first weight being greater than the second weight.

The generating the integrated pulse wave signal may include integrating the plurality of pulse wave signals by applying the weight to each of the plurality of pulse wave signals to obtain weighted pulse wave signals, and by summing up the weighted pulse wave signals.

BRIEF DESCRIPTION OF THE DRAWINGS

The above and/or other aspects will be more apparent by describing certain example embodiments, with reference to the accompanying drawings, in which.

DETAILED DESCRIPTION

Figure 1:
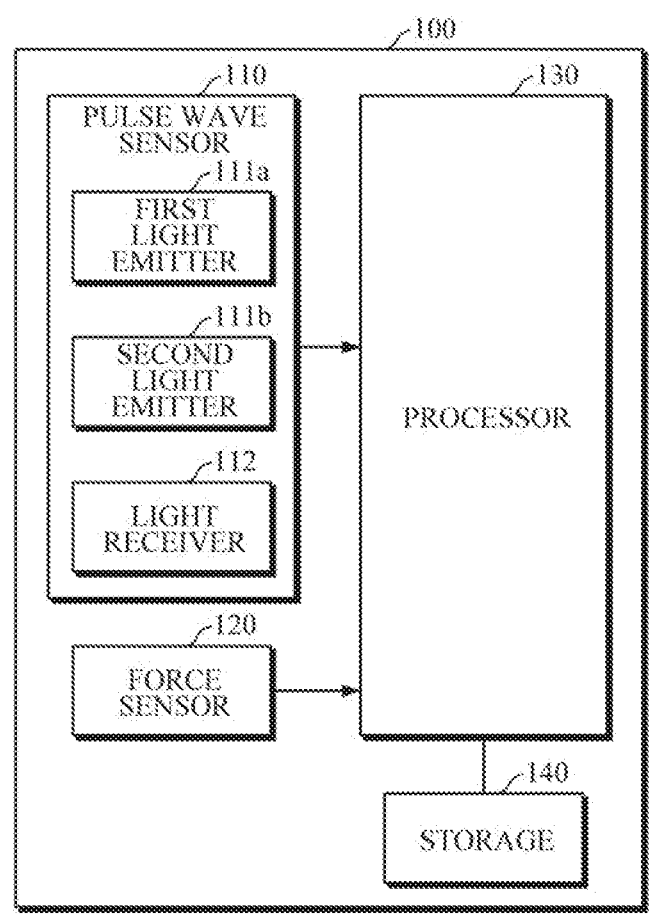
FIG. 1 is a block diagram illustrating an apparatus for measuring bio-information according to an example embodiment.

Example embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the example embodiments. However, it is apparent that the example embodiments can be practiced without those specifically defined matters. Also, well-known functions or constructions are not described in detail since they would obscure the description with unnecessary detail.

Process steps described herein may be performed differently from a specified order, unless a specified order is clearly stated in the context of the disclosure. That is, each step may be performed in a specified order, at substantially the same time, or in a reverse order.

Further, the terms used throughout this specification are defined in consideration of the functions according to exemplary embodiments, and can be varied according to a purpose of a user or manager, or precedent and so on. Therefore, definitions of the terms should be made on the basis of the overall context.

It will be understood that, although the terms first, second, etc. may be used herein to describe various elements, these elements should not be limited by these terms. These terms are only used to distinguish one element from another. Any references to singular may include plural unless expressly stated otherwise. In the present specification, it should be understood that the terms, such as 'including' or 'having,' etc., are intended to indicate the existence of the features, numbers, steps, actions, components, parts, or combinations thereof disclosed in the specification, and are not intended to preclude the possibility that one or more other features, numbers, steps, actions, components, parts, or combinations thereof may exist or may be added.

Expressions such as "at least one of" when preceding a list of elements, modify the entire list of elements and do not modify the individual elements of the list. For example, the expression, "at least one of a, b, and c," should be understood as including only a, only b, only c, both a and b, both a and c, both b and c, all of a, b, and c, or any variations of the aforementioned examples.

Further, components that will be described in the specification are discriminated merely according to functions mainly performed by the components. That is, two or more components which will be described later can be integrated into a single component. Furthermore, a single component which will be explained later can be separated into two or more components. Moreover, each component can additionally perform some or all of a function executed by another component in addition to the main function thereof. Some or all of the main function of each component can be carried out by another component. Each component may be implemented as hardware, software, or a combination of both.

Figure 2:
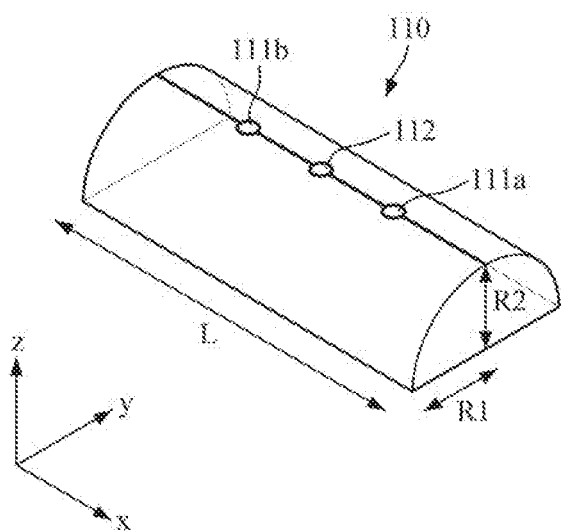
FIG. 2 is a diagram illustrating a structure of a pulse wave sensor according to an example embodiment.
Figure 3:
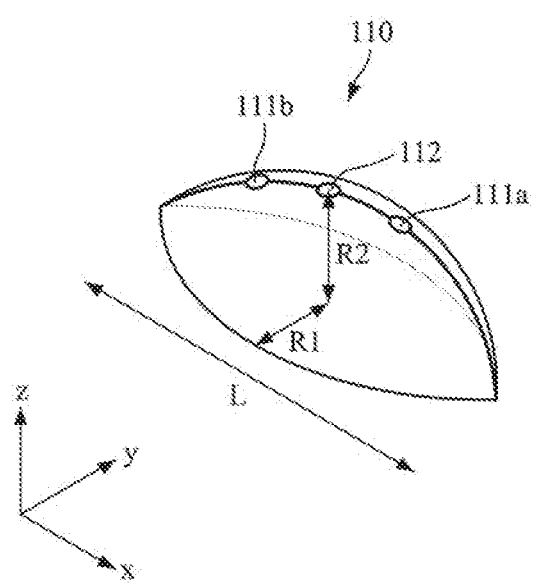
FIG. 3 is a diagram illustrating a structure of a pulse wave sensor according to another example embodiment.
Figure 4:
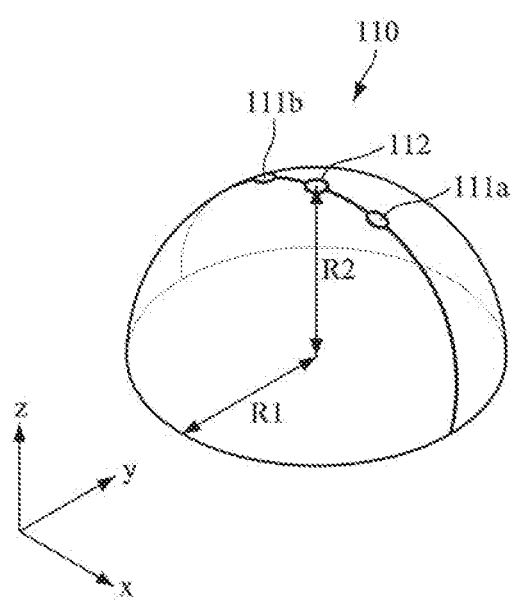
FIG. 4 is a diagram illustrating a structure of a pulse wave sensor according to another example embodiment.

FIG. 1 is a block diagram illustrating an apparatus for measuring bio-information according to an example embodiment, and FIGS. 2, 3 and 4 are diagrams illustrating structures of pulse wave sensors according to example embodiments. The apparatus 100 for measuring bio-information of FIG. 1 may be embedded in an electronic device, electronic device accessories (e.g., protective case for the electronic device, etc.), a stylus pen, a joystick, and the like. In particular, examples of the electronic device may include a cellular phone, a smartphone, a tablet PC, a laptop computer, a personal digital assistant (PDA), a portable multimedia player (PMP), a navigation device, an MP3 player, a digital camera, a wearable device, and the like; and examples of the wearable device may include a wristwatch-type wearable device, a wristband-type wearable device, a ring-type wearable device, a waist belt-type wearable device, a necklace-type wearable device, an ankle band-type wearable device, a thigh band-type wearable device, a forearm band-type wearable device, and the like. However, the electronic device is not limited to the above examples, and the wearable device is neither limited thereto.

Referring to FIG. 1, the apparatus 100 for measuring bio-information includes a pulse wave sensor 110, a force sensor 120, a processor 130, and a storage 140.

The pulse wave sensor 110 may measure a plurality of pulse wave signals from an object which is in contact with the pulse wave sensor 110. The pulse wave signal may be a photoplethysmogram (PPG) signal. The object may be a body part which may come into contact with the pulse wave sensor 110, and may be a body part where the pulse wave signals may be easily measured. For example, the object may be a distal portion of the body, such as fingers, toes, and the like, or an area on the wrist which is adjacent to the radial artery and an upper portion of the wrist where veins or capillaries are located. For convenience of explanation, the following description will be given using a finger as an example of the object.

In consideration of the elasticity and anatomy of the finger, the pulse wave sensor 110 may be formed to have a contact surface, which is curved convexly toward a finger being in contact with the contact surface. In one embodiment, the pulse wave sensor 110 may have a semi-cylindrical shape as illustrated in FIG. 2, a semi-elliptical shape as illustrated in FIG. 3, or a semi-spherical shape as illustrated in FIG. 4. In this case, a contract surface of the pulse wave sensor 110 may have a size smaller than a size of the finger (e.g., a known average size of a finger), so that a contact area between the finger and the pulse wave sensor 110 may be fixed and constant. Since the size of the contact surface of the pulse wave sensor 110 is less than the size of the finger, the contact area between the finger and the pulse wave sensor 110 may be equal to the area of entire contact surface of the pulse wave sensor 110. The apparatus 100 may store, in the storage 140, the area of the contact surface of the pulse wave sensor 110 as the contact area between the finger and the pulse wave sensor 110, so that the apparatus 100 is able to estimate a contact pressure by using a force sensor 120, without a measurement of a contact area between the finger and the pulse wave sensor 110.

With reference to FIG. 2, for example, the pulse wave sensor 110 may have a first radius of curvature R1 in a range of between 2 mm and 10 mm and a second radius of curvature R2 in a range of between 0.5*R1 and 4*R1. In a case in which the pulse wave sensor 110 has a semi-cylindrical shape and/or a semi-elliptical shape, a length L of the pulse wave sensor 10 may be less than or equal to 16 mm by considering the width of the finger.

By using such structure of the pulse wave sensor 110, pressure may be transmitted into the inner part of the finger effectively with less force compared to a flat surface structure. Further, in order to obtain bio-information accurately, the apparatus 100 for measuring bio-information may need to be accurately and closely in contact with an object (e.g., blood vessels, etc.) so that bio-information can be obtained from the object, and the above structure of the pulse wave sensor 110 may enable the apparatus 100 for measuring bio-information to easily obtain information on the inner part of the finger (e.g., blood vessels and blood in the finger, etc.).

The pulse wave sensor 110 includes a first light emitter 111a and a second light emitter 111b and a light receiver 112.

The first and second light emitters 111a and 111b may emit light of a predetermined wavelength onto the finger. For example, light of the predetermined wavelength may include visible light and infrared light (e.g., light in a wavelength range of 400 nm to 900 nm), and the like, but is not limited thereto. That is, wavelengths of light emitted by the first and second light emitters 111a and 111b may vary depending on the purpose of measurement. Further, the first and second light emitters 111a and 111b are not necessarily formed of a single light source, and may be formed of an array of a plurality of light sources. In a case in which the first and second light emitters 111a and 111b are formed of an array of a plurality of light sources, all the plurality of light sources may emit light of different wavelengths, or some of the light sources may emit light of the same wavelength and others may emit light of different wavelengths. In one embodiment, the first and second light emitters 111a and 111b may include a light emitting diode (LED), a laser diode, a phosphor, and the like.

The light receiver 112 may receive light, emitted by the first light emitter 111a and returning from the object, to measure a first pulse wave signal, and may receive light, emitted by the second light emitter 111b and returning from the object, to measure a second pulse wave signal. In one embodiment, the light receiver 112 may include a photo diode, a photo transistor (PTr), an image sensor (including a charge-coupled device (CCD), a Complementary Metal-Oxide Semiconductor (CMOS), etc.), and the like. The light receiver 112 is not necessarily formed of a single device, and may be formed of an array of a plurality of devices.

The light receiver 112 may be disposed at the center of a curved surface which is a contact surface, and the first and second light emitters 111a and 11b may be symmetrically disposed with respect to the light receiver 112 in a longitudinal direction of the pulse wave sensor 110 or in a tangential direction of the curved surface. The light receiver 112 may be disposed between the first and second light emitters 111a and 111b along a same straight line. In this case, in order to reduce the effect of an edge on pressure or force, the first and second light emitters 111a and 111b may be disposed at an inner portion (e.g., in a range of 0.1 L to 0.9 L being the length of the pulse wave sensor) rather than an edge portion. For example, as illustrated in FIG. 2, in the case where the pulse wave sensor 110 has a semi-cylindrical shape, the light receiver 112 may be disposed at the center of the curved surface, i.e., in the middle of a tangent line of the curved surface, and the first and second light emitters 111a and 111b may be symmetrically disposed with respect to the light receiver 112 in a longitudinal direction of the pulse wave sensor 110 or a tangential direction of the curved surface. In another example, as illustrated in FIG. 3, in a case in which the pulse wave sensor 110 has a semi-elliptical shape, the light receiver 112 may be disposed at the center of the curved surface, and the first and second light emitters 111a and 111b may be symmetrically disposed with respect to the light receiver 112 in a longitudinal direction of the pulse wave sensor 110. In yet another example, as illustrated in FIG. 4, in the case where the pulse wave sensor 110 has a semi-spherical shape, the light receiver 112 may be disposed at the center of the curved surface, and the first and second light emitters 111a and 111b may be symmetrically disposed with respect to the light receiver 112. However, these are merely examples, and the structure of the light emitters and the light receiver is not limited thereto.

While FIGS. 1 to 4 illustrate the pulse wave sensor 110 including one light receiver and a pair of light emitters, this is merely for convenience of explanation, and the pulse wave sensor 110 is not limited thereto. That is, the pulse wave sensor 110 may include one light receiver, and two or more pairs of light emitters which are symmetrically disposed with respect to the light receiver, and may include a plurality of optical sensors including one light receiver and one or more pairs of light emitters which are symmetrically disposed with respect to the light receiver.

The force sensor 120 may measure a contact force that is applied by the object into the pulse wave sensor 110. To this end, the force sensor 120 may include an acceleration sensor, a piezoelectric film, a load cell, radar, a strain gauge, and the like.

In an example embodiment, the force sensor 120 may be disposed above or below the pulse wave sensor 110. In the case where the force sensor 120 is disposed above the pulse wave sensor 110, the force sensor 120 may be made of a light transmitting material.

In another example embodiment, in order to allow a user to press the pulse wave sensor 110 and the force sensor 120 with one finger at the same time, the force sensor 120 may be disposed adjacent to the pulse wave sensor 110.

In yet another example embodiment, the force sensor 120 may be disposed at a position, adjacent to the first and second light emitters 111a and 111b or the light receiver 112, on the curved surface of the pulse wave sensor 110. In this case, the first and second light emitters 111a and 111b, the light receiver 112, and the force sensor 120 may be disposed adjacent to each other, so that the user may press them with one finger at the same time.

The processor 130 may control the overall operation of the apparatus 100 for measuring bio-information, and may be composed of one or more processors, a memory, and a combination thereof.

The processor 130 may control the pulse wave sensor 110 to measure a plurality of pulse wave signals required for measuring bio-information. Upon receiving a request for measuring bio-information from a user, the processor 130 may generate a control signal for controlling the pulse wave sensor, and may control the pulse wave sensor 110 based on the control signal. In one embodiment, the pulse wave sensor 110 may measure a plurality of pulse wave signals by simultaneously or sequentially driving the first and second light emitters 111a and 111b according to predetermined driving conditions of the first and second light emitters 111a and 111b. In this case, the driving conditions of each of the first and second light emitters 111a and 111b may include an emission time, a driving sequence, a current intensity, a pulse duration, and the like of each light emitter, and may be pre-stored in an internal or external storage device of the processor 130.

The processor 130 may generate guide information on contact force to be increased or decreased by the user for the pulse wave sensor 110 while the pulse wave signal is measured, and may provide the guide information for the user. The guide information includes information of a recommend contact force that may be required to measure the pulse wave signal. The processor 130 may visually display the guide information on contact force, or may display the guide information by a non-visual method using voice, vibrations, and the like.

The guide information on contact force may be provided before and after, or at the same time as, a time when the pulse wave sensor 110 starts to measure the pulse wave signal. The guide information on contact force may be provided continuously while the pulse wave sensor 110 measures the pulse wave signal from the object. The guide information on contact force may be predetermined for each user based on user characteristics such as a user's age, sex, health condition, a contact portion of the object, and the like. The guide information on contact force may be a force value itself, which is to be increased or decreased by the user for the pulse wave sensor 110, but is not limited thereto, and may include information on a user's action for inducing the user to change force to be applied by the object to the pulse wave sensor 110.

Upon receiving a request for measuring bio-information, the processor 130 may generate a control signal to control the force sensor 120 to measure a contact force between the object and the pulse wave sensor 110.

The processor 130 may continuously receive measured contact force values from the force sensor 120, and may generate the guide information on contact force based on the received measured contact force values and provide the guide information for the user. For example, the processor 130 may provide guide information on contact pressure based on a difference between a contact force measurement value, which is measured at a specific time, and a contact force value to be applied by the user to the pulse wave sensor 110 at the specific time.

The processor 130 may generate an integrated pulse wave signal by integrating a plurality of pulse wave signals based on the measured contact force. In one embodiment, the processor 130 may determine a center of force (Cof) of the measured contact force, may determine a weight to be applied to each pulse wave signal based on the determined center of force, and may integrate the plurality of pulse wave signals by applying the determined weight to each pulse wave signal.

For example, the processor 130 may determine the center of force of the measured contact force by using the following Equation 1.

$$Cof(Cof_x, Cof_y) = \left(\frac{-T_y + F_x \times L}{F_z}, \frac{-T_x + F_y \times L}{F_z}\right) \quad \text{[Equation 1]}$$

Herein, $Cof_x$ and $Cof_y$ denote an X axis directional component and a Y axis directional component of the center of force; $F_x$, $F_y$, and $F_z$ denote contact force values in an X axis direction, a Y axis direction, and a Z axis direction, respectively; $T_x$ and $T_y$ denote an X axis directional torque and a Y axis directional torque, respectively; and L denotes the length of the pulse wave sensor.

The processor 130 may apply a greater weight to a pulse wave signal, measured by using a light emitter which is located closer to the center of force, than a pulse wave signal measured by using a light emitter which is located further from the center of force. For example, the processor 130 may determine a weight to be applied to each pulse wave signal by using the following Equation 2.

$$W_a = \frac{Cof_x}{L} + 0.5, \quad W_b = 1 - W_a. \quad \text{[Equation 2]}$$

Herein, $W_a$ denotes a weight to be applied to the pulse wave signal measured by using the light emitter located closer to the center of force, and $W_b$ denotes a weight to be applied to the pulse wave signal measured by using the light emitter located further from the center of force. For example, when the pulse wave sensor 110 obtains a first pulse wave signal PPGa and a second pulse wave signal PPGb from the first and second light emitters 111a and 111b, respectively, and the first light emitter 111a is located closer to the center of force than the second light emitter 111b, Wa is applied to the first pulse wave signal PPGa and Wb is applied to the second pulse wave signal PPGb.

By applying the weight to each pulse wave signal, and summing up the weighted pulse wave signals, the processor 130 may generate an integrated pulse wave signal. For example, the processor 130 may generate the integrated pulse wave signal by integrating the plurality of pulse wave signals using the following Equation 3.

$$PPG_{comb} = W_a \times PPG_a + W_b \times PPG_b \quad \text{[Equation 3]}$$

Herein, $PPG_a$ denotes the pulse wave signal measured by using the light emitter located closer to the center of force, and $PPG_b$ denotes the pulse wave signal measured by using the light emitter located further from the center of force.

The processor 130 may determine contact pressure between the finger and the pulse wave sensor 110 based on the measured contact force and a contact area between the finger and the pulse wave sensor 110. Since the pulse wave sensor 110 may have a size smaller than a size of the finger so that a contact area between the finger and the pulse wave sensor 110 may be constant, the contact area between the finger and the pulse wave sensor 110 may be equal to an area of the curved surface of the pulse wave sensor 110. The processor 130 may retrieve information of the area of the curved surface of the pulse wave sensor 110 from the storage 140, as information of the contact area between the finger and the pulse wave sensor 110. The processor 130 may determine the contact pressure by dividing the contact force by the area of the curved surface.

The processor 130 may estimate bio-information by analyzing the contact pressure and the integrated pulse wave signal. In this case, bio-information may include blood pressure, blood glucose, cholesterol, vascular age, arterial stiffness, aortic pressure waveform, vascular compliance, blood triglyceride, cardiac output, total peripheral resistance, stress index, degree of fatigue, and the like. However, for convenience of explanation, the following description will be given using blood pressure as an example of bio-information.

Blood pressure may include Diastolic Blood Pressure (DBP), Systolic Blood Pressure (SBP), and Mean Arterial Pressure (MAP). The contact pressure applied to the finger may act as an external pressure on the blood vessels. If the contact pressure is lower than the MAP, an elastic restoring force of tissues act to constrict the blood vessels, such that the amplitude of the pulse wave signal is reduced. If the contact pressure is equal to the MAP, the elastic restoring force of tissues becomes zero, having no effect on the blood vessels, such that the amplitude of the pulse wave signal reaches its peak value. Further, if the contact pressure is greater than the MAP, the elastic restoring force of tissues act to dilate the blood vessels, such that the amplitude of the pulse wave signal is reduced. Accordingly, by analyzing the change of the integrated pulse wave signal according to the contact pressure, the processor 130 may estimate, as the MAP, a contact pressure value at a point where an amplitude value of the integrated pulse wave signal is maximum. Further, the processor 130 may estimate, as the systolic blood pressure (SBP), a contact pressure value at a point where a ratio of an amplitude value to the maximum amplitude value is a first ratio (e.g., 0.6); and may estimate, as the diastolic blood pressure (DBP), a contact pressure value at a point where a ratio of an amplitude value to the maximum amplitude is a second ratio (e.g., 0.7).

Figure 5:
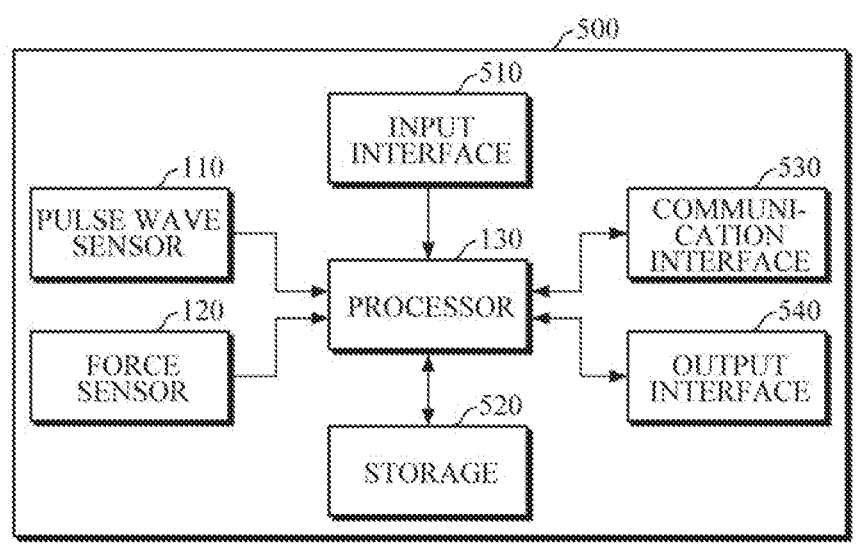
FIG. 5 is a block diagram illustrating an apparatus for measuring bio-information according to another example embodiment.

FIG. 5 is a block diagram illustrating an apparatus for measuring bio-information according to another example embodiment. The apparatus 500 for measuring bio-information of FIG. 5 may be embedded in an electronic device, electronic device accessories (e.g., protective case for the electronic device, etc.), a stylus pen, a joystick, and the like. Examples of the electronic device may include a cellular phone, a smartphone, a tablet PC, a laptop computer, a personal digital assistant (PDA), a portable multimedia player (PMP), a navigation device, an MP3 player, a digital camera, a wearable device, and the like. Examples of the wearable device may include a wristwatch-type wearable device, a wristband-type wearable device, a ring-type wearable device, a waist belt-type wearable device, a necklace-type wearable device, an ankle band-type wearable device, a thigh band-type wearable device, a forearm band-type wearable device, and the like. However, the electronic device is not limited to the above examples, and the wearable device is neither limited thereto.

Referring to FIG. 5, the apparatus 500 for measuring bio-information includes the pulse wave sensor 110, the force sensor 120, the processor 130, an input interface 510, a storage 520, a communication interface 530, and an output interface 540. Here, the pulse wave sensor 110, the force sensor 120, and the processor 130 are described above with reference to FIGS. 1 to 4, such that a detailed description thereof will be omitted.

The input interface 510 may receive input of various operation signals from a user. In one embodiment, the input interface 510 may include a keypad, a dome switch, a touch pad (static pressure/capacitance), a jog wheel, a jog switch, a hardware (H/W) button, and the like. Particularly, the touch pad, which forms a layer structure with a display, may be called a touch screen.

The storage 520 may store programs or commands for operation of the apparatus 500 for measuring bio-information, and may store data input to and output from the apparatus 500 for measuring bio-information. Further, the storage 520 may store data processed by the apparatus 500 for measuring bio-information, and data required for data processing by the apparatus 500 for measuring bio-information. For example, the storage 520 may store an area of a contract surface of the pulse wave sensor 110.

The storage 520 may include at least one storage medium of a flash memory type memory, a hard disk type memory, a multimedia card micro type memory, a card type memory (e.g., an SD memory, an XD memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like. Further, the apparatus 500 for measuring bio-information may operate an external storage medium, such as web storage and the like, which performs a storage function of the storage 520 on the Internet.

The communication interface 530 may perform communication with an external device. For example, the communication interface 530 may transmit, to the external device, the data used by the apparatus 500 for measuring bio-information, processing result data of the apparatus 500 for measuring bio-information, and the like; or may receive, from the external device, various data required or useful for measuring a pulse wave signal and contact pressure and/or estimating bio-information.

In this case, the external device may be medical equipment using the data used by the apparatus 500 for measuring bio-information, the processing result data of the apparatus 500 for measuring bio-information, and the like, a printer to print out results, or a display to display the results. In addition, the external device may be a digital TV, a desktop computer, a cellular phone, a smartphone, a tablet PC, a laptop computer, a personal digital assistant (PDA), a portable multimedia player (PMP), a navigation device, an MP3 player, a digital camera, a wearable device, and the like, but is not limited thereto.

The communication interface 530 may communicate with an external device by using Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, WIFI communication, Radio Frequency Identification (RFID) communication, 3G communication, 4G communication, 5G communication, and the like. However, this is merely an example and is not intended to be limiting.

The output interface 540 may output the data used by the apparatus 500 for measuring bio-information, the processing result data of the apparatus 500 for measuring bio-information, and the like. In one embodiment, the output interface 540 may output the data used by the apparatus 500 for measuring bio-information, the processing result data of the apparatus 500 for measuring bio-information, and the like by using at least one of an acoustic method, a visual method, and a tactile method. To this end, the output interface 540 may include a display, a speaker, a vibrator, and the like.

Figure 6:
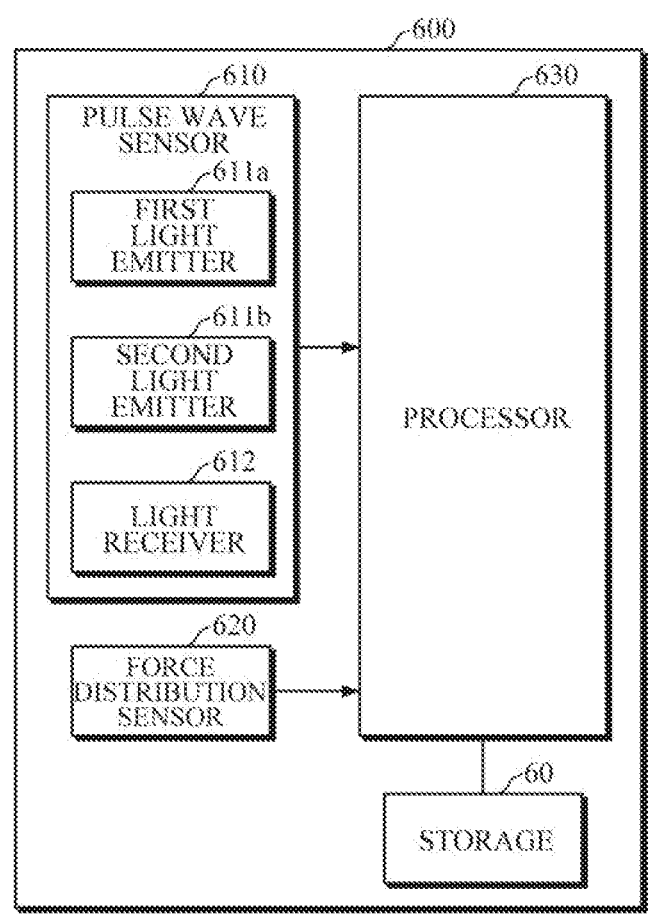
FIG. 6 is a block diagram illustrating an apparatus for measuring bio-information according to another example embodiment.
Figure 7:
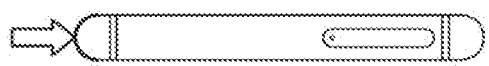
FIG. 7 is a diagram illustrating an example of an apparatus for measuring bio-information.
Figure 8:
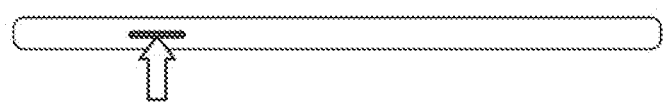
FIG. 8 is a diagram illustrating another example of an apparatus for measuring bio-information.
Figure 9:
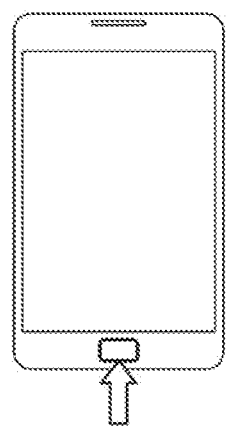
FIG. 9 is a diagram illustrating yet another example of an apparatus for measuring bio-information.
Figure 10:
FIG. 10 is a diagram illustrating still another example of an apparatus for measuring bio-information.
Figure 11:
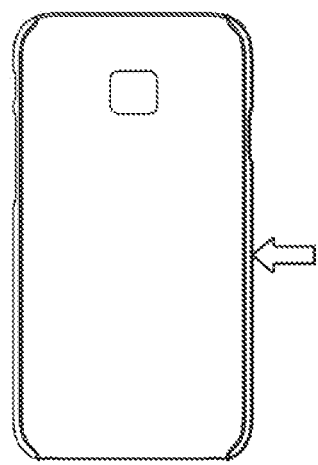
FIG. 11 is a diagram illustrating still another example of an apparatus for measuring bio-information.
Figure 12:
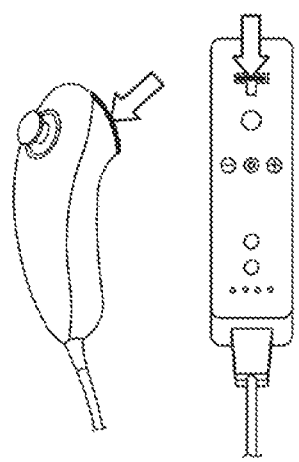
FIG. 12 is a diagram illustrating still another example of an apparatus for measuring bio-information.

FIG. 6 is a block diagram illustrating an apparatus for measuring bio-information according to another example embodiment. The apparatus 600 for measuring bio-information of FIG. 6 may be embedded in an electronic device, electronic device accessories (e.g., protective case for the electronic device, etc.), a stylus pen, a joystick, and the like. In this case, examples of the electronic device may include a cellular phone, a smartphone, a tablet PC, a laptop computer, a personal digital assistant (PDA), a portable multimedia player (PMP), a navigation device, an MP3 player, a digital camera, a wearable device, and the like; and examples of the wearable device may include a wristwatch-type wearable device, a wristband-type wearable device, a ring-type wearable device, a waist belt-type wearable device, a necklace-type wearable device, an ankle band-type wearable device, a thigh band-type wearable device, a forearm band-type wearable device, and the like. However, the electronic device is not limited to the above examples, and the wearable device is neither limited thereto.

Referring to FIG. 6, the apparatus 600 for measuring bio-information includes a pulse wave sensor 610, a force distribution sensor 620, a processor 630, and a storage 640. Here, the pulse wave sensor 610, the processor 630, and the storage 640 are substantially the same as or similar to the pulse wave sensor 110, the processor 130, and the storage 140 described above with reference to FIGS. 1 to 5, such that a detailed description thereof will be omitted to avoid redundancy.

The force distribution sensor 620 may measure distribution of contact force that is applied by the object to the pulse wave sensor 610 and is distributed along a contact surface of the pulse wave sensor 610. To this end, the force distribution sensor 620 may include a force sensor, an optical sensor, and the like, but is not limited thereto, and may include various sensors for directly or indirectly measuring three distribution. The force sensor may include an acceleration sensor, a piezoelectric film, a load cell, radar, a strain gauge, and the like. The optical sensor may measure force distribution based on an absorbance difference. For example, as force increases, an amount of a reflector (e.g., blood) at a corresponding position is reduced and absorbance increases, such that it can be seen that force at a position having a high absorbance may be greater than force at a position having a low absorbance. Based on this principle, the optical sensor may measure distribution of contact force between the object and the pulse wave sensor 610. The force distribution sensor 620 may emit a plurality of lights to a plurality of different positions on a contact surface of the pulse wave sensor 610, so that the plurality of lights are transmitted to a different positions under the skin of the object, and may receive the plurality of lights when the plurality of lights are scattered or reflected from the object. The force distribution sensor 620 may measure an absorbance of each of the received plurality of lights, and may determine a contact force distribution based on the absorbance of each of the received plurality of lights. The force distribution sensor 620 may determine that a stronger force is applied to a first position of the contact surface at which a light having a relatively high absorbance is obtained, than a second position of the contact surface at which a light having a relatively low absorbance is obtained.

In one embodiment, the force distribution sensor 620 may include at least one light emitter and at least one light receiver, separately from the pulse wave sensor 610, or alternatively, may use a first light emitter 611a, a second light emitter 611b, and a light receiver 612 of the pulse wave sensor 610 to emit/receive the plurality of lights to/from the plurality of different positions of the object. The force distribution sensor 620 may be integrated into the processor 630, and the processor 630 may determine the contact force distribution based on the absorbance of each of the received plurality of lights.

The processor 630 may generate an integrated pulse wave signal by integrating a plurality of pulse wave signals based on the measured contact force distribution. In one embodiment, the processor 630 may determine a weight to be applied to each pulse wave signal based on the measured contact force distribution, and may integrate a plurality of pulse wave signals by applying the determined weight to each pulse wave signal.

In one embodiment, the processor 630 may apply a greater weight to a pulse wave signal, measured by using a light emitter (e.g., the first light emitter 611a) located at a position having a greater contact force, than a pulse wave signal measured by using a light emitter (e.g., the second light emitter 611b) located at a position having a smaller contact force. For example, the processor 630 may determine the weight to be applied to each pulse wave signal by using the following Equation 4.

$$W_1 = \frac{F_1}{F_1 + F_2}, \quad W_2 = \frac{F_2}{F_1 + F_2} \quad \text{[Equation 4]}$$

Herein, $W_1$ and $W_2$ each denote a weight to be applied to a first pulse wave signal measured by using the first light emitter 611a, and a weight to be applied to a second pulse wave signal measured by using the second light emitter 611b; and $F_1$ and $F_2$ each denote distribution of force applied to an area of the first light emitter 611a and distribution of force applied to an area of the second light emitter 611b.

The processor 630 may apply the determined weight to each pulse wave signal, and may generate an integrated pulse wave signal by summing up the weighted pulse wave signals. For example, the processor 630 may generate the integrated pulse wave signal by integrating the plurality of pulse wave signals using the following Equation 5.

$$PPG_{comb} = W_1 \times PPG_1 + W_1 \times PPG_1 \quad \text{[Equation 5]}$$

Herein, $PPG_1$ denotes the first pulse wave signal measured using the first light emitter 611a, and $PPG_2$ denotes the second pulse wave signal measured using the second light emitter 611b.

Equations 4 and 5 may be applied to an example of using two pulse wave signals which are measured by two light emitters. In the case of using n number of pulse wave signals measured by using n number of light emitters, Equations 4 and 5 may be expressed by the following Equations 6 and 7 respectively.

$$W_i = \frac{F_i}{\sum F} \quad \text{[Equation 6]}$$

$$PPG_{comb} = W_1 \times PPG_1 + W_2 \times PPG_2 + \ldots + W_n \times PPG_n \quad \text{[Equation 7]}$$

Herein, i denotes an index of the light emitter or the pulse wave signal.

The processor 630 may determine contact pressure between the finger and the pulse wave sensor 610 based on the measured contact force distribution, and a contact area between the finger and the pulse wave sensor 610. For example, the processor 630 may determine a maximum value or a mean value of the contact force, and may determine contact pressure by dividing the maximum value or the mean value of the contact force by an area of a curved surface.

The processor 130 may estimate bio-information by analyzing the contact pressure and the integrated pulse wave signal. In this case, bio-information may include blood pressure, blood glucose, cholesterol, vascular age, arterial stiffness, aortic pressure waveform, vascular compliance, blood triglyceride, cardiac output, total peripheral resistance, stress index, degree of fatigue, and the like.

FIGS. 7 to 13 are diagrams illustrating examples of apparatuses for measuring bio-information.

Figure 13:
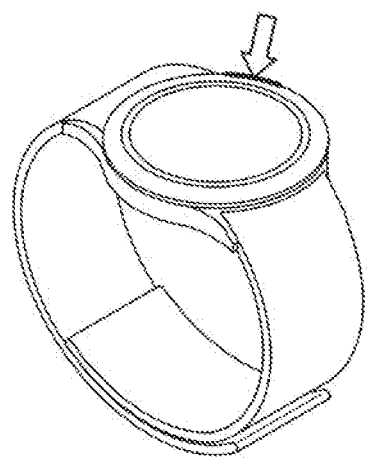
FIG. 13 is a diagram illustrating still another example of an apparatus for measuring bio-information.

The apparatuses 100, 500, and 600 for measuring bio-information may be applied to an edge of a smartphone (see FIG. 7), a side button of a smartphone (see FIG. 8), a home button of a smartphone (see FIG. 9), a button or a frame of a stylus pen (see FIG. 10), an edge of a protective case for a smartphone (see FIG. 11), a button or an edge of a joystick (see FIG. 12), and an edge of a wristwatch-type wearable device (see FIG. 13).

FIGS. 7 to 13 are merely examples and the apparatuses 100, 500, and 600 for measuring bio-information are not limited thereto. That is, the apparatuses 100, 500, and 600 for measuring bio-information may be applied, without limitation, to any curved surface or a button formed at an electronic device, electronic device accessories (e.g., a protective case for the electronic device, etc.), a stylus pen, a joystick, and the like.

Figure 14:
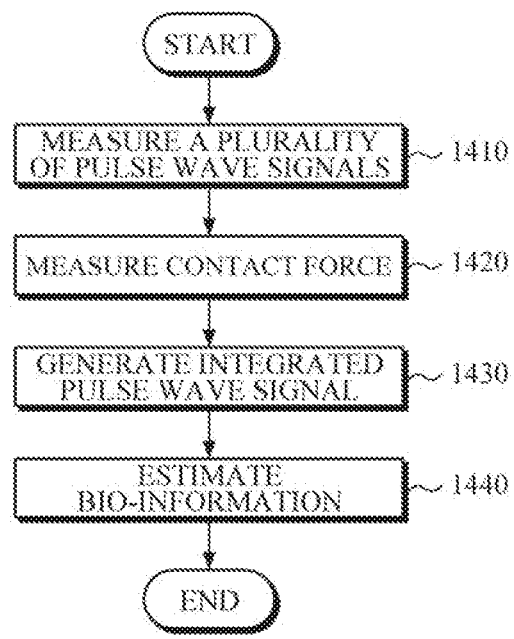
FIG. 14 is a flowchart illustrating a method of measuring bio-information according to an example embodiment.

FIG. 14 is a flowchart illustrating a method of measuring bio-information according to an example embodiment. The method of measuring bio-information of FIG. 14 may be performed by the apparatuses 100 and 500 for measuring bio-information of FIGS. 1 and 5.

Referring to FIG. 14, the apparatus for measuring bio-information may measure a plurality of pulse wave signals from a finger which is in contact with a contact surface of the pulse wave sensor which is a curved surface in operation 1410. Here, the pulse wave signal may be a PPG signal. In one embodiment, the apparatus for measuring bio-information may emit light onto the finger, which is in contact with a contact surface formed as a curved surface, and may measure a plurality of pulse wave signals by receiving light returning from the finger.

The apparatus for measuring bio-information may measure a contact force between the finger and the pulse wave sensor in operation 1420.

The apparatus for measuring bio-information may generate an integrated pulse wave signal by integrating the plurality of pulse wave signals based on the measured contact force in operation 1430. In one embodiment, the apparatus for measuring bio-information may determine a center of force (Cof) of the measured contact force, may determine a weight to be applied to each pulse wave signal based on the determined center of force, and may integrate the plurality of pulse wave signals by applying the determined weight to each pulse wave signal. For example, the apparatus for measuring bio-information may determine the center of force of the contact force by using Equation 1, and may determine the weight to be applied to each pulse wave signal by using Equation 2. Further, the apparatus for measuring bio-information may generate the integrated pulse wave signal by applying the weight to each pulse wave signal and by summing up the weighted pulse wave signals by using Equation 3.

The apparatus for measuring bio-information may estimate bio-information by analyzing the measured contact force and the integrated pulse wave signal in operation 1440. For example, the apparatus for measuring bio-information may determine contact pressure between the finger and the pulse wave sensor based on the measured contact force and the contact area between the finger and the pulse wave sensor, and may estimate bio-information by analyzing the contact pressure and the integrated pulse wave signal. In this case, bio-information may include blood pressure, blood glucose, cholesterol, vascular age, arterial stiffness, aortic pressure waveform, vascular compliance, blood triglyceride, cardiac output, total peripheral resistance, stress index, degree of fatigue, and the like.

Figure 15:
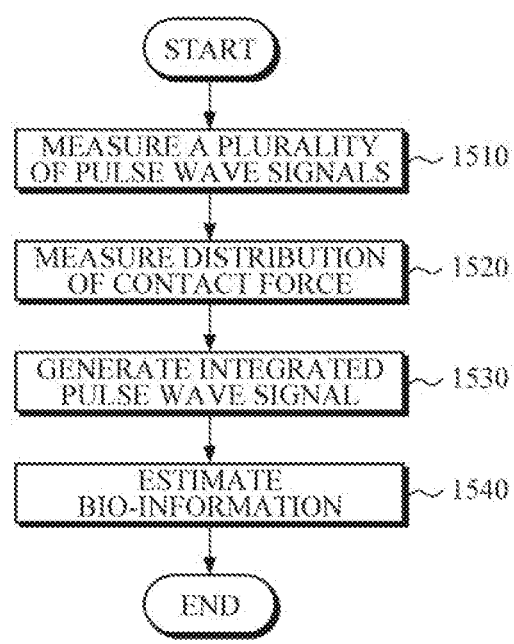
FIG. 15 is a flowchart illustrating a method of measuring bio-information according to another example embodiment.

FIG. 15 is a flowchart illustrating a method of measuring bio-information according to another example embodiment. The method of measuring bio-information of FIG. 15 may be performed by the apparatus 600 for measuring bio-information.

Referring to FIG. 15, the apparatus for measuring bio-information may measure a plurality of pulse wave signals from a finger being in contact with a contact surface of the pulse wave sensor which is a curved surface in operation 1510. Here, the pulse wave signal may be a PPG signal. In one embodiment, the apparatus for measuring bio-information may emit light onto the finger, which is in contact with a contact surface formed as a curved surface, and may measure a plurality of pulse wave signals by receiving light returning from the finger.

The apparatus for measuring bio-information may measure distribution of contact force between the finger and the pulse wave sensor in operation 1520.

The apparatus for measuring bio-information may generate an integrated pulse wave signal by summing up the plurality of pulse wave signals based on the measured contact force distribution in operation 1530. In one embodiment, the apparatus for measuring bio-information may determine a weight to be applied to each pulse wave signal based on the measured contact force distribution, and may integrate the plurality of pulse wave signals by applying the determined weight to each pulse wave signal. For example, the apparatus for measuring bio-information may determine the weight to be applied to each pulse wave signal by using Equation 4 or 6, and may generate an integrated pulse wave signal by applying the determined weight to each pulse wave signal and by summing up the weighted pulse wave signals by using Equation 5 or 7.

The apparatus for measuring bio-information may estimate bio-information by analyzing the measured contact force distribution and the integrated pulse wave signal in operation 1540. For example, the apparatus for measuring bio-information may determine contact pressure between the finger and the pulse wave sensor based on the measured contact force distribution and the contact area between the finger and the pulse wave sensor, and may estimate bio-information by analyzing the contact pressure and the integrated pulse wave signal. In this case, bio-information may include blood pressure, blood glucose, cholesterol, vascular age, arterial stiffness, aortic pressure waveform, vascular compliance, blood triglyceride, cardiac output, total peripheral resistance, stress index, degree of fatigue, and the like.

While not restricted thereto, an example embodiment can be embodied as computer-readable code on a computer-readable recording medium. The computer-readable recording medium is any data storage device that can store data that can be thereafter read by a computer system. Examples of the computer-readable recording medium include read-only memory (ROM), random-access memory (RAM), CD-ROMs, magnetic tapes, floppy disks, and optical data storage devices. The computer-readable recording medium can also be distributed over network-coupled computer systems so that the computer-readable code is stored and executed in a distributed fashion. Also, an example embodiment may be written as a computer program transmitted over a computer-readable transmission medium, such as a carrier wave, and received and implemented in general-use or special-purpose digital computers that execute the programs. Moreover, it is understood that in example embodiments, one or more units of the above-described apparatuses and devices can include circuitry, a processor, a microprocessor, etc., and may execute a computer program stored in a computer-readable medium.

The foregoing embodiments are merely examples and are not to be construed as limiting. The present teaching can be readily applied to other types of apparatuses. Also, the description of the example embodiments is intended to be illustrative, and not to limit the scope of the claims, and many alternatives, modifications, and variations will be apparent to those skilled in the art.

What is claimed is:

1. An apparatus for measuring bio-information, the apparatus comprising:
    a pulse wave sensor comprising at least one pair of light emitters which are disposed apart from each other and a light receiver disposed between the at least one pair of light emitters, the pulse wave sensor being configured to measure a plurality of pulse wave signals from a subject by using the light receiver and the at least one pair of light emitters;
    a force sensor configured to measure a contact force that is applied to the pulse wave sensor by the subject;
    a memory configured to store size information of a mathematical area of a contact surface of the pulse wave sensor, wherein an entire surface of the contact surface is configured to be in contact with the subject; and
    a processor configured to:
        retrieve the size information of the mathematical area of the contact surface of the pulse wave sensor from the memory;
        generate an integrated pulse wave signal by integrating the plurality of pulse wave signals;
        determine contact pressure based on the contact force and the mathematical area of the contact surface of the pulse wave sensor; and
        estimate bio-information of the subject based on the integrated pulse wave signal and the contact pressure.

2. The apparatus of claim 1, wherein the contact surface of the pulse wave sensor is a curved surface.

3. The apparatus of claim 2, wherein the light receiver is disposed under the curved surface and aligned at a center of the curved surface.

4. The apparatus of claim 3, wherein the at least one pair of light emitters is disposed in a longitudinal direction of the pulse wave sensor or in a tangential direction of the curved surface, and
    wherein the at least one pair of light emitters is arranged in a range of 0.1 L to 0.9 L from the center of the curved surface, and L denotes a length of the pulse wave sensor in the longitudinal direction.

5. The apparatus of claim 1, wherein the processor is further configured to:
    determine a center of the contact force based on a first contact force in an X-axis direction, a second contact force in a Y-axis direction, a third contact force in a Z-axis direction, and a length of the pulse wave sensor, and integrate the plurality of pulse wave signals by applying a weight to each of the plurality of pulse wave signals based on the determined center of the contact force.

6. The apparatus of claim 5, wherein the at least one pair of light emitters comprises a first light emitter and a second light emitter, and the first light emitter is disposed closer to the center of the contact force than the second light emitter,
    wherein the plurality of pulse wave signals comprises a first pulse wave signal measured by using the first light emitter and a second pulse wave signal measured by using the second light emitter, and
    wherein the processor is further configured to apply a first weight to the first pulse wave signal that is measured by using the first light emitter which is located closer to the center of the contact force than the second light emitter, and apply a second weight to the second pulse wave signal that is measured by using the second light emitter which is located further from the center of the contact force than the first light emitter, the first weight being greater than the second weight.

7. The apparatus of claim 5, wherein the processor is further configured to generate the integrated pulse wave signal by applying the weight to each of the plurality of pulse wave signals to obtain weighted pulse wave signals, and by summing the weighted pulse wave signals.

8. The apparatus of claim 1, wherein the plurality of pulse wave signals are photoplethysmogram (PPG) signals.

9. The apparatus of claim 1, wherein the processor is further configured to generate guide information on a recommended contact force based on the contact force which is measured by the force sensor.

10. The apparatus of claim 1, wherein the bio-information comprises at least one of blood pressure, blood glucose, cholesterol, vascular age, arterial stiffness, aortic pressure waveform, vascular compliance, blood triglyceride, cardiac output, total peripheral resistance, stress index, and degree of fatigue.

11. A method of measuring bio-information, the method comprising:
    measuring, by a pulse wave sensor, a plurality of pulse wave signals from a subject, the pulse wave sensor comprising at least one pair of light emitters which are disposed apart from each other and a light receiver disposed between the at least one pair of light emitters;
    measuring a contact force that is applied to the pulse wave sensor by the subject;
    retrieving size information of a mathematical area of a contact surface of the pulse wave sensor from a memory, wherein an entire surface of the contact surface is configured to be in contact with the subject,
    generating an integrated pulse wave signal by integrating the plurality of pulse wave signals;
    determining contact pressure based on the contact force and the mathematical area of the contact surface of the pulse wave sensor; and
    estimating bio-information of the subject based on the integrated pulse wave signal and the contact pressure.

12. The method of claim 11, wherein the generating the integrated pulse wave signal comprises:
- determining a center of the contact force based on a first contact force in an X-axis direction, a second contact force in a Y-axis direction, a third contact force in a Z-axis direction, and a length of the pulse wave sensor; and
- integrating the plurality of pulse wave signals by applying a weight to each of the plurality of pulse wave signals based on the determined center of the contact force.

13. The method of claim 12, wherein the measuring the plurality of pulse wave signals comprises measuring a first pulse wave signal by using a first light emitter of the pair of light emitters and the light receiver, and measuring a second pulse wave signal by using a second light emitter of the pair of light emitters, wherein the first light emitter is disposed closer to the center of the contact force than the second light emitter, and wherein the integrating the plurality of pulse wave signals comprises applying a first weight to the first pulse wave signal that is measured by using the first light emitter which is located closer to the center of the contact force, and applying a second weight to the second pulse wave signal measured by using the second light emitter which is located further from the center of the contact force than the first light emitter, the first weight being greater than the second weight.

14. The method of claim 12, wherein the integrating the plurality of pulse wave signals comprises applying the weight to each of the plurality of pulse wave signals to obtain weighted pulse wave signals, and by summing the weighted pulse wave signals.

15. The method of claim 11, wherein the plurality of pulse wave signals are photoplethysmogram (PPG) signals.

16. The method of claim 11, wherein the bio-information comprises at least one of blood pressure, blood glucose, cholesterol, vascular age, arterial stiffness, aortic pressure waveform, vascular compliance, blood triglyceride, cardiac output, total peripheral resistance, stress index, and degree of fatigue.

* * * * *